(12) United States Patent
Chesneau

(10) Patent No.: US 7,803,625 B2
(45) Date of Patent: Sep. 28, 2010

(54) METHOD FOR DETERMINING THE FATTY ACID PROFILE OF MILK BY INFRARED SPECTROSCOPY

(75) Inventor: Guillaume Chesneau, Combourtille (FR)

(73) Assignee: Valorex, Combourtille (FR)

( * ) Notice: Subject to any disclaimer, the term of this patent is extended or adjusted under 35 U.S.C. 154(b) by 0 days.

(21) Appl. No.: 12/303,321

(22) PCT Filed: Jun. 1, 2007

(86) PCT No.: PCT/FR2007/000917

§ 371 (c)(1), (2), (4) Date: Dec. 10, 2008

(87) PCT Pub. No.: WO2007/141416

PCT Pub. Date: Dec. 13, 2007

(65) Prior Publication Data

US 2009/0197340 A1 Aug. 6, 2009

(30) Foreign Application Priority Data

Jun. 7, 2006 (FR) ................................. 06 05075

(51) Int. Cl.
*G01N 33/06* (2006.01)
(52) U.S. Cl. .......................................... 436/23; 436/71
(58) Field of Classification Search .................. 436/20, 436/23
See application file for complete search history.

(56) References Cited

U.S. PATENT DOCUMENTS 5,343,044 A * 8/1994 Sjaunja et al. ......... 250/339.09
2005/0250212 A1 11/2005 Azizian
2005/0250213 A1 * 11/2005 Azizian ........................ 436/71

FOREIGN PATENT DOCUMENTS

WO 00/39578 A2 7/2000

OTHER PUBLICATIONS

Mossoba et al. "Application of Standard Addition to Eliminate Conjugated Linoleic Acid and Other Interferences in the Determination of the Total Trans Fatty Acids in Selected Food Products by Infrared Spectroscopy," Journal of the American Oil Chemists' Society 2001: 78: 631-634.*
Li et al. "Trans Determination of Edible Oils by Fourier Transform Near-Infrared Spectroscopy," Journal of the American Oil Chemists' Society 2000: 77: 1061-1067.*
Foss Analytical Catalog, "MilkoScanTM TF2," Issue 1, Great Britain, Feb. 2006.*
Azizian and Kramer "A Rapid Method for the Quantification of Fatty Acids in Fats and Oils with Emphasis on trans Fatty Acids Using Fourier Transform Near Infrared Spectroscopy (FT-NIR)" Lipids 2005, 40, 855-867.*
Soyeurt et al. "Variation in Fatty Acid Contents of Milk and Milk Fat Within and Across Breeds," J. Dairy Sci. 2006, 89, 4858-4865.*
Juaneda et al. "Analytical methods for determination of trans fatty acid content in food," Eur. J. Lipid Sci. Technol. 2007, 109, 901-917.*
Bartlet et al. Detection of Hydrogenated Fats by Measurement of cis-trans Conjugated Unsaturation. J. Agric. Food Chem. 1961, 9, 50-53.*
Azizian, H. et al. "Quantification of trans fatty acids in food products by GC, ATR-FTIR and FT-NIR methods", Lipid Technology, vol. 16, No. 10, Oct. 2004, pp. 229-231.
Soyeurt, H. et al. "Estimating Fatty Acid Content in Cow Milk Using Mid-Infrared Spectrometry", Journal of Dairy Science, vol. 89, No. 9, Sep. 2006, pp. 3690-3695.

* cited by examiner

*Primary Examiner*—Yelena G Gakh
*Assistant Examiner*—Michelle M Adams
(74) *Attorney, Agent, or Firm*—Novak Druce + Quigg; J. Rodman Steele, Jr.; Gregory M. Lefkowitz

(57) ABSTRACT

The nutritional quality of milk lipids is determined by a method for predicting percentages of minor fatty acids in milk. A database is created by correlating known fatty acid profiles of reference milk samples obtained by gas phase chromatography to mid-infrared spectra to obtain calibrations, wherein the calibrations vary in accuracy from one fatty acid to another. The determination of a milk fatty acid profile to be analyzed through infrared treatment is limited to some fatty acids with a satisfactory calibration. Equations to predict the percentages of minor fatty acids are developed using correlations of fatty acids with satisfactory calibrations.

16 Claims, No Drawings

METHOD FOR DETERMINING THE FATTY ACID PROFILE OF MILK BY INFRARED SPECTROSCOPY

This invention relates to a method for determining the nutritional quality of milk lipids, involving the steps of considering a defined number of reference milk samples; determining, for each of the reference samples, a fatty acid profile and an infrared spectrum obtained through reflection on the reference sample of mid-infrared radiation and associating respectively the fatty acid profiles with the infrared spectra, subjecting the milk to be analyzed, the lipid nutritional quality of which is to be determined, to infrared radiation, so as, through reflection, to infer an infrared spectrum, and comparing the infrared spectrum of the milk to be analyzed to the infrared spectra of the reference samples, so as to infer a fatty acid profile of the milk to be analyzed.

The method relies on the pairing, or the association, of a fatty acid and a mid-infrared wavelength corresponding to the radiation reflected by the considered acid and reflecting therefore the existence thereof.

Dairy products are the first quantitative source of lipids in man's diet. In the form of butter, cheese, milk drink and other fresh products, dairy products supply, in France for example, more than 30 g of fatty acids of a total of 100 g per adult, per day.

However, the milk fat does not have a very good reputation in human nutrition and has incurred for many years a decrease in consumption. Milk producers are continuously searching for valorization and differentiation means, which leads them today to be interested in the quality of their fat material.

In contrast with vegetable oils, containing some twenty different major fatty acids, milk fat materials are made of a very high number of different fatty acids.

Approximately 400 different fatty acids are known in milk lipids. The relative proportions of such fatty acids are extremely variable depending on numerous parameters: the cow breed, the individual, the season, the lactation stage, the calving number and primarily, the cows' diet.

The two main milk fatty acids are a saturated fatty acid: palmitic acid (C16:0), and an unsaturated fatty acid: oleic acid (C18:1 n-9). Those two fatty acids account for approximately 50% of milk fatty acids. The proportions thereof in the total fatty acids are extremely variable. The palmitic acid accounts for 18 to 45% of the total fatty acids. The oleic acid accounts for 12 to 35% of the total fatty acids.

In addition to those two fatty acids, milk also contains:
 a. short chain saturated fatty acids (number of carbon atoms in the chain ranging from 2 to 10);
 b. medium chain saturated fatty acids: lauric acid (C12:0) and myristic acid (C14:0);
 c. cis- and trans-monoene fatty acids (mainly the C18:1 trans11 vaccenic acid);
 d. conjugated fatty acids (mainly conjugated linoleic acid (CLA) cis9, trans11);
 e. branched fatty acids;
 f. polyunsaturated fatty acids of the Omega 3 family (mainly alpha-linolenic acid C18:3 n-3);
 g. polyunsaturated fatty acids of the Omega 6 family (mainly linolenic acid C18:2 n-6).

The wide variety and the large dispersion of the composition of milk fatty acids on the one hand, and the quantitative amount of the consumption of milk lipids on the other hand, make very important the evaluation of the nutritional quality of milk lipids.

For nutritionists, there are no good fatty acids and bad fatty acids in man's diet, but only excess fatty acids and deficient ones. All nutritional guidelines agree to recommend the following:
 a. an increase in the consumption of (C18:1 n-9) oleic acid,
 b. an increase in the consumption of (C18:3 n-3) alpha-linolenic acid,
 c. a limitation in the consumption of (C16:0) palmitic acid,
 d. a limitation in the consumption of (C18:2 n-6) linoleic acid,
 e. an increase in the C18:1 n-9/C16:0 ratio,
 f. a decrease in the C18:2 n-6/C18:3 n-3 ratio.

Interesting effects would be also attributed to the consumption of conjugated (CLA cis9, trans11) fatty acids.

Thus, it seems to be most interesting to be able to evaluate, rapidly and completely, the nutritional quality of milk lipids through their fatty acid profile.

Such an evaluation is very difficult for numerous reasons:
 a. the number of milk fatty acids to be measured,
 b. the large variation of the fatty acid composition (for example, the values as measured for the Omega 3 alpha-linolenic acid range from 0.1% to 2% as a function of milks),
 c. the difficulties and the cost of the analytical techniques being used (gas phase chromatography).

Model for Determining the Fatty Acid Composition of Milk Lipids a. Introduction

Determining the fatty acids profile of milk lipids occurs using the gas phase chromatography (GPC). It makes it possible to separate gas mixtures as a result of a balance between a mobile gas phase and a stationary phase. The method relates to naturally volatile molecules, but also to molecules not being subjected to temperatures that do not cause the decomposition thereof.

Chronologically, the method relies on:
 1—a step for extracting the fatty material,
 2—a preparation of methyl esters of fatty acids,
 3—an analysis through gas phase chromatography of such methyl esters of fatty acids.

The period and the cost of such a determination method make it hard to be operational for milk producers searching for valorization of the milk fatty material through its nutritional quality.

So, a method has been contemplated, being equally reliable, but faster and less expensive: the infrared analysis.

b. Equipment

The infrared Fourier transform (FTIR) equipment allows for spectral definition in the infrared.

The FTIR equipment working in the near infrared, at wavelengths in the range of 1000 to 2500 nm, can be used for determining fatty acid profiles of different oils or solid foodstuffs. However, it has two major disadvantages:
 the method is not accurate and lacks resolution, since the characteristical wavelengths of the different fatty acids overlap;
 it is poorly adapted for liquid products, for which a perfect control of the temperature is required.

In addition to the gas phase chromatography and the analysis in the near infrared, the Applicant thus proposes today an analysis in the mean infrared, at wavelengths ranging from 2500 to 10,000 nm.

This is a bold evolution insofar as the infrared analysis was not satisfactory.

The determination method of this invention consists in first creating a database determining the infrared spectra of a high number of samples of reference milk having a known fatty acid profile determined by the gas phase chromatography method.

Otherwise stated, the Applicant have considered a large number of samples of reference milk and worked fatty acid by fatty acid.

For each fatty acid, they have selected a plurality of reference samples with a determined content via GPC. They have irradiated said samples with a mid-IR radiation and obtained, through reflection, as many spectra as samples of reference milk in the fatty acid being considered. Such spectra overlap in a point—or a small area of wavelengths—corresponding to the wavelength of the fatty acid under consideration.

Working similarly for all the selected fatty acids consists in calibrating the determination method. The more the overlapping areas of the spectra are small and point-like, the more the calibration becomes powerful or accurate.

The database is therefore made of a plurality of sets with four elements (fatty acid, content, wavelength, calibration power). The content may be the molecular percentage of the fatty acid under consideration on the total of fatty acids.

Incidentally, the Applicant have used as the FTIR equipment, the FT 6000 device from the Foss company. It is well adapted for milk and shows a good stability.

The measurement is performed through analyzing the mid-infrared transmission signal through the sample located in a measurement cell. The selected optical system is made of a Michelson interferometer. The resulting whole signal is afterwards broken down through Fourier transform so as to obtain the complete sample absorption spectrum.

Such a spectrum is directly related to the whole chemical composition of the sample and is thus not specific to such or such other molecule, although are within the mid-infrared field specific absorption areas of characteristic C—H, C=O, C—OH or N—H. links of the organic chemistry present in the sample.

The development consists thus in searching within the spectra for the weight of the absorptions of each of the wavelengths allowing for the fatty acid under study to be defined.

It is understood that the quality of an infrared calibration, for analyzing new milk samples, i.e. for determining the nutritional quality of the lipids thereof, strongly depends on the quality of the database used for this purpose. The latter depends on the number and the representative state of the samples constituting it as well as on the quality of the values obtained for the compounds searched for by the reference method. In addition, such a databank should cover the whole measurement range being contemplated and the reference samples should represent all the different matrices being likely to be subjected to the trial.

The database as implemented by the Applicant comprises approximately 150 reference milk samples coming from quite various breeding areas (West, East, North and South of France), milk cattle (races, genetics, production level, . . . ), seasons (Spring, Winter) and food intake systems (full food intake, semi-full food intake, . . . ) and diet systems (corn ensilage, pasture grass, graze ensilage, ribboned graze, hay, alfalfa, energy and protein concentrates, lipid supply source), such systems being representative of all the production modes and taking into account every variation factor of the quality of milk lipids.

Such reference samples, treated in the mid-infrared, produce characteristic spectra in a given wavelength or in a sufficiently narrow band for being well distinguished from the others.

The Applicant, in view of the above presented statements, have thus realized that the power, or the accuracy, of the calibration varied from one fatty acid to another and that it could be satisfactory for one and not for another. Thus, for the C16:0 palmitic acid, with enough samples, the accuracy of the calibration may reach 90%, or even higher, but for the fatty acids from the Omega 3 family, this is not the case.

This is why the Applicant also realizing that the proportions of the various fatty acids were correlated therebetween have also contemplated making the most of such a correlation, in order to define regression prediction equations, for example, a linear regression, and thus determine the content of some fatty acids from that of other fatty acids determined via infrared treatment with a better accuracy and thus limit the determination of the fatty acid profile of the milk to be analyzed through infrared treatment to some fatty acids with a satisfactory calibration.

Hereinbelow, there is presented an example of the determination of the composition of a milk sample in minor fatty acids (AG) statistically predicted through regression from the determination in major fatty acids through infrared treatment.

The determination is set forth from the table of prediction equations hereinbelow, wherein AGS stands for the saturated fatty acids,
AGI " the unsaturated fatty acids,
AGPI " the polyunsaturated fatty acids,
AGMI " for the monounsaturated fatty acids,
and
r the result accuracy (correlation coefficient).

Prediction Equations $$AGS+AGI=100; r=1.00$$

$$AGPI+AGMI=AGI; r=1.00$$

$$AGMI=0.672+0.852*AGI; r=0.98$$

$$C14:0=18.284-0.256*C18:1\ totals; r=0.80$$

$$C16:0=35.35+0.231*AGS-0.587*AGI; r=0.87$$

$$C18:1\ totals=1.032*AGMI-5.157; r=0.98$$

$$C18:1\ cis\ totals=0.76*C18:1\ totals+0.646*AGMI-0.554*AGI+2.512; r=0.98$$

$$C18:1\ cis\text{-}9=1.143*018:1\ cis\ totals-0.204*AGI-0.031*C18:1\ totals+2.028; r=0.99$$

$$C18:1\ totals=C18:1\ cis\ totals+C18:1\ trans\ totals; r=1.00$$

$$C18:3=0.005*AGI+0.193*AGPI-0.01*C16:0-0.09\ (\text{when } C16:0>25.5\%); r=0.86$$

$$C18:3=11.917e^{(-0.1041 C16:0)}\ (\text{when } C16:0<25.5\%); r=0.83$$

$$CLA\ cis9,trans11=0.366*AGPI-0.381*C18:3-0.364; r=0.78$$

$$C18:1\ trans\ totals=0.477*CLA\ cis9,trans11-0.043*AGS+1.362*C18:1\ trans11+3.428; r=0.96$$

$$C18:2=0.657*AGPI-0.718*C18:3-0.006*AGI-0.477*CLA\ cis9,trans11+0.292; r=0.80$$

$$C18:1\ trans\text{-}11=2.319*CLA\ cis9,trans11+0.409*C18:3-0.109*AGPI+0.034; r=0.94$$

$$C18:1\ trans10=0.438*C18:1\ trans\ totals+0.091*CLA\ cis9,trans11-0.556*C18:1\ trans11-0.114; r=0.94$$

The different prediction parameters in the above presented table between the different milk fatty acids were checked and validated in relation to known synthesis mechanisms of milk fatty acids in cows' rumen and udder.

EXAMPLE OF DETERMINATION OF THE NUTRITIONAL QUALITY OF MILK LIPIDS

1. Determination through infrared treatment of saturated milk fatty acids (AGS),
2. Determination through dissimilarity of unsaturated fatty acids (AGI) AGI=100−AGS
3. Predictive determination through linear regression of milk mono-unsaturated fatty acids (AGMI):

$AGMI=0.672+0.852*AGI$, with a result accuracy $r=0.98$

4. Determination through dissimilarity of polyunsaturated fatty acids (AGPI) AGPI=AGI−AGMI
5. Determination through infrared treatment of milk C16:0 and C18:1 totals
6. Predictive determination through linear regression of milk C14:0

$C14:0=18.284-0.256*C18:1$ totals $r=0.80$

7. Predictive determination through linear regression of milk C18:3 n-3

$C18:3=0.005*AGI+0.193*AGPI-0.01*C16:0-0.029$ $r=0.86$

8. Predictive determination through linear regression of milk CLA c9 t11 (or CLA1)

$CLA1=0.366*AGPI-0.381*C18:3-0.364$ $r=0.78$

9. Predictive determination through linear regression of milk C18:2 n-6

$C18:2=0.657*AGPI-0.718*C18:3-0.006*AGI-0.477*CLA1+0.292$ $r=0.80$

10. Predictive determination through linear regression of milk C18:0

$C18:0=0.146*AGI-0.006*C18:1$ totals$+2.041*C18:3+4.92$ $r=0.628$

11. Predictive determination through linear regression of milk C18:1 t11

$C18:1$ trans$11=2.319*CLA1+0.409*C18:3-0.109*AGPI+0.034$ $r=0.94$

12. Predictive determination through linear regression of milk C18:1 totals $C18:1$ cis totals$=0.76*C18:1$ totals$+0.646*AGMI-0.554*AGI+2.512$ $r=0.98$ 13. Predictive determination through linear regression of milk C18:1 cis9

$C18:1$ cis$9=1.143*C18:1$ cis totals$-0.204*AGI-0.031*C18:1$ totals$+2.028$ $r=0.99$ 14. Predictive determination through linear regression of milk C18:1 trans totals $C18:1$ trans totals$=0.477*CLA1-0.043*AGS+1.362*C18:1$ trans$11+3.428$ $r=0.96$ 15. Predictive determination through linear regression of milk C18:1 trans 10

$C18:1$ trans$10=0.438*C18:1$ trans totals$+0.091*CLA1-0.556*C18:1$ trans$11-0.114$ $r=0.94$ By means of the above described analysis technique, it is possible to rapidly know the nutritional quality of the lipids from the above described milk the very day of its production.

The milk producers and the dairy industry thus have available a very reliable, very fast and very practical to use tool that will make it possible to accelerate the method for improving the nutritional quality of milk lipids.

The invention claimed is:

1. A method for determining the nutritional quality of milk lipids, involving the steps consisting of
    considering a defined number of reference milk samples with known fatty acid profiles determined through gas phase chromatography;
    creating a database by subjecting said reference milk samples to mid-infrared radiation to obtain reference spectra and associating respectively said reference spectra to said known fatty acid profiles to develop calibrations, wherein the calibrations vary in accuracy from one fatty acid to another, and wherein the calibrations comprise satisfactory calibrations from major fatty acids in the known fatty acid profiles;
    subjecting a test milk sample to be analyzed for lipid nutritional quality to mid-infrared radiation to obtain a sample spectrum;
    comparing said sample spectrum to the reference spectra to infer a sample fatty acid profile, wherein said sample fatty acid profile is limited to percentages of the major fatty acids in the known fatty acid profiles with satisfactory calibrations;
    developing prediction equations to correlate the percentages of the major fatty acids in the known fatty acid profiles with satisfactory calibrations to percentages of minor fatty acids in the known fatty acid profiles; and
    predicting percentages of minor fatty acids in the test milk sample using the prediction equations and the sample fatty acid profile.

2. A method according to claim 1, wherein the database comprises a plurality of sets with four elements comprising a fatty acid, the percentage of said fatty acid, a wavelength, and a calibration power.

3. A method according to claim 1, wherein the percentage of saturated fatty acids (AGS) in the test milk sample is determined through infrared spectroscopy and wherein the major fatty acids in the known fatty acid profile with satisfactory calibrations comprise C16:0 and C18:1 total fatty acids (C18:1 totals).

4. A method according to claim 3, wherein the percentage of unsaturated fatty acids (AGI) in the test milk sample is predicted with a prediction equation of AGI=100−AGS.

5. A method according to claim 4, wherein the percentage of milk mono-unsaturated fatty acids (AGMI) in the test milk sample is predicted with a prediction equation of AGMI=0.672+0.852*AGI.

6. A method according to claim 5, wherein the percentage of polyunsaturated fatty acids (AGPI) in the test milk sample is predicted with a prediction equation of AGPI=AGI−AGMI.

7. A method according to claim 3, wherein the percentage of C14:0 fatty acids (C14:0) in the test milk sample is predicted with a prediction equation of C14:0=18.284−0.256*C18:1 totals.

8. A method according to claim 3, wherein the percentage of C18:3 n-3 fatty acids (C18:3 n-3) in the test milk sample is predicted with a prediction equation of (C18:3 n-3)=0.005*AGI+0.193*AGPI−0.01*C16:0−0.029, wherein AGI=100−AGS, AGPI=AGI−AGMI, and AGMI=0.672+0.852*AGI.

9. A method according to claim 8, wherein the percentage of conjugated linoleic acid cis9, trans11 fatty acids (CLA1) in the test milk sample is predicted with a prediction equation of CLA1=0.366*AGPI−0.381*(C18:3 n-3)−0.364.

10. A method according to claim 9, wherein the percentage of C18:2 n-6 fatty acids (C18:2 n-6) in the test milk sample is predicted with a prediction equation of (C18:2 n-6)=0.657*AGPI−0.718*C18:3−0.006*AGI−0.477*CLA1+0.292.

11. A method according to claim 3, wherein the percentage of C18:0 fatty acids (C18:0) in the test milk sample is predicted with a prediction equation of C18:0=0.146*AGI−0.006*C18:1 totals+2.041*C18:3+4.92, wherein AGI=100−AGS and (C18:3 n-3)=0.005*AGI+0.193*AGPI−0.01*C16:0−0.029.

12. A method according to claim 11, wherein the percentage of C18:1 trans11 fatty acids (C18:1 trans11) in the test milk sample is predicted with a prediction equation of C18:1 trans11=2.319*CLA1+0.409*(C18:3 n-3)−0.109*AGPI+0.034.

13. A method according to claim 3, wherein the percentage of C18:1 cis totals total fatty acids (C18:1 cis totals) in the test milk sample is predicted with a prediction equation of C18:1 cis totals=0.76*(C18:1 totals)+0.646*AGMI−0.554*AGI+2.512, AGMI=0.672+0.852*AGI, and AGI=100−AGS.

14. A method according to claim 13, wherein the percentage of C18:1 cis9 total fatty acids (C18:1 cis9) in the test milk sample is predicted with a prediction equation of C18:1 cis9=1.143*(C18:1 cis totals)−0.204*AGI−0.031*(C18:1 totals)+2.028.

15. A method according to claim 12, wherein the percentage of C18:1 trans total fatty acids (C18:1 trans totals) in the test milk sample is predicted with a prediction equation of C18:1 trans totals=0.477*CLA1−0.043*AGS+1.362*(C18:1 trans11)+3.428, wherein CLA1=0.366*AGPI−0.381*(C18:3 n-3)−0.364.

16. A method according to claim 15, wherein the percentage of C18:1 trans10 fatty acids (C18:1 trans10) in the test milk sample is predicted with a prediction equation of C18:1 trans10=0.438*(C18:1 trans totals)+0.091*CLA1−0.556*(C18:1 trans11)−0.114.

* * * * *